US008277853B2

(12) United States Patent
Van Kempen et al.

(10) Patent No.: US 8,277,853 B2
(45) Date of Patent: Oct. 2, 2012

(54) COMPOSITION FOR HAIR AND BODY APPLICATION

(75) Inventors: Dallas Van Kempen, San Marcos, CA (US); Don Van, San Marcos, CA (US)

(73) Assignee: Eqyss Grooming Products, Carlsbad, CA (US)

( * ) Notice: Subject to any disclaimer, the term of this patent is extended or adjusted under 35 U.S.C. 154(b) by 0 days.

(21) Appl. No.: 11/953,854

(22) Filed: Dec. 10, 2007

(65) Prior Publication Data

US 2008/0085252 A1 Apr. 10, 2008

Related U.S. Application Data

(63) Continuation-in-part of application No. 11/253,968, filed on Oct. 19, 2005, now abandoned.

(51) Int. Cl.
*A61K 36/886* (2006.01)

(52) U.S. Cl. ........................................................ 424/744

(58) Field of Classification Search .......................... None
See application file for complete search history.

(56) References Cited

U.S. PATENT DOCUMENTS

| 5,208,011 A * | 5/1993 | Vaughan ........................ 424/59 |
| 5,393,520 A * | 2/1995 | Incando ..................... 424/70.13 |
| 5,804,168 A * | 9/1998 | Murad ............................ 424/59 |
| 5,935,556 A * | 8/1999 | Tanner et al. .................. 424/59 |
| 2002/0071818 A1 * | 6/2002 | Cole et al. .................... 424/70.1 |

OTHER PUBLICATIONS

SPA Hair Conditioner. Internet Archive Date: Mar. 24, 2004 [Retrieved from the Internet on: Sep. 28, 2008]. Retrieved from:<http://web.archive.org/web/20040324101349/http://www.deadseacosmetic.com/spahaco250ml. html>.*

* cited by examiner

*Primary Examiner* — Amy L Clark
(74) *Attorney, Agent, or Firm* — Katherine M. Bond, Esq.; Sheldon Mak & Anderson PC

(57) ABSTRACT

The present invention relates to a novel composition and method using the same for topical application to mammalian subject's skin or hair particularly useful for promoting hair health and more particularly hair growth.

1 Claim, No Drawings

COMPOSITION FOR HAIR AND BODY APPLICATION

RELATED APPLICATIONS

This Continuation in Part application claims the benefit of priority of U.S. application Ser. No. 11/253,968 filed Oct. 19, 2005, which claims the benefit of priority of U.S. Provisional Application No. 60/522,603 filed Oct. 19, 2004, which is incorporated herein by reference.

FIELD OF THE INVENTION

The present invention relates to a composition and method for treating hair and
skin and more particularly to a composition for application to hair for repairing damage to skin, nails and hair.

Hair loss or alopecia is a common problem in both males and females regardless of their age. There are several types of hair loss, such as androgenetic alopecia, alopecia greata, telogen effluvium, hair loss due to systemic medical problems, e.g., thyroid disease, adverse drug effects and nutritional deficiency states as well as hair loss due to scalp or hair trauma, discoid lupus erythematosus, lichen planus and structural shaft abnormalities. (Hogan and Chamberlain, 2000). Of the above, androgenetic alopecia is the most common cause of hair loss, affecting about 30% of individuals who have a strong family history of hair loss. (Bergfeld, 1988). Androgenetic alopecia is caused by three interdependent factors: male hormone dihydrotestosterone (DHT), genetic disposition and advancing age. DHT causes hair follicles to degrade and further shrink in size, resulting in weak hairs. DHT also shortens the anagen phase of the hair follicle growing cycle. Over time, more hairs are shed and hairs become thinner. Possible options for the treatment of alopecia include reassurance, hair prosthesis, surgery and topical/oral medications. (Hogan & Chamberlain, 2000; Bertolino, 1993; Setty, 1970).

The most common pharmacological management of androgenetic alopecia is topical minoxidil and finasteride taken orally. The main problem with topical minoxidil therapy is patient compliance, although it has been shown to be effective in a few studies. (DeVillez et al, 1994; Trancik R J, 1998). On the other hand, oral finasteride is associated with significant adverse effects such as decreased libido, impotence and ejaculation disorders. (Chen et al, 1996).

In addition, there is a report by Goldman et al. (1996) which evaluates whether male pattern baldness is associated with a deficiency in oxygen supply to body tissue. The results indicate that penetration of oxygen was lower in the bald frontal scalp than in hair-bearing temporal scalp area. As such, good blood supply to the scalp is essential to maintain normal cycle of hair growth.

Significant attention is devoted in the art, to providing proper skin care including nutrients to through lotions and creams, yet little or no attention is devoted to the follicles, which feed the hair. Indeed, scant devotion is afforded the scalp and its particular nutritional needs. The present invention fulfils this need through providing beneficial tocopherol, a valuable anti-oxidant, castor oil a moisturizing and therapeutic oil, and keratin to promote simultaneously the healing of damaged hair including hair follicles and generation of new hair growth.

Keratin is the protein hair is made of and may be essential for proper growth and strength of new hair. Castor oil is a thick oil which assists the scalp and hair in water retention, thereby increasing hair and scalp health and vitality.

Vitamin E, tocopheryl acetate is a potent anti-oxidant and has been found useful in combating many health problems. While there was a report of the beneficial effects of vitamin E in hair care products (Shipp, 1994), its potential in the restoration of hair growth has yet to be explored.

Accordingly, there is a need for a composition which combines a tocopherol eg, a Vitamin E and a caster oil to promote hair growth and health of the hair and the scalp.

SUMMARY OF THE INVENTION

Accordingly it is an object of the present invention to provide compositions that impart benefits such as moisturizing and repair to hair and scalp and other body areas to which they are applied.

In an exemplary embodiment, the inventive compositions comprise a deionized water base of weight percent ranging from 55% to 95.7%, 0.30 to 0.35 weight percent of one or more preservatives selected from the group consisting of DMDM hydantoin, methylparaben, and polyparaben, 0.05 to 0.10 weight percent of a chelating agent, 0.001 to 5.05 weight percent of one or more conditioners and/or moisturizers selected from the group consisting of polyquatemium-10, polyethylene glycol derivative of lanolin, cetrimonium chloride, cetrimonium bromide, Crotein HKPTM, mixed mucopolysaccharides, pyrrolidone carboxylic acid, propylene glycol, hydrolyzed keratin protein, aloe Vera powder, 0.05 to 0.15 weight percent of an antioxidant selected from the group consisting of citric acid and vitamin E acetate and a heavy oil such as caster oil. Further embodiments of the inventive composition include one or more anti-inflammatory agents, one or more antiseptics, stabilizers and emulsifiers. The composition, which is in liquid form, may be applied in the form of a spray or mist directly to the hair and scalp, or by pouring a small amount of the liquid into the hand for application or directly onto the affected area, such as the hair and scalp.

DETAILED DESCRIPTION OF THE INVENTION

The above and other objects are achieved by a hair treatment product for protecting hair against damage secondary to heat drying, against environmental influences and hair treatments as well as for protecting other components of hair against oxidation and degradation, said hair treatment product comprising in an aqueous phase a mixture of (a) castor oil and (b) oil soluble tocopherols, both components having an affinity to hair. Many additional ingredients may be included as is known in the art of hair care, including the following:

Stearalkonium Chloride, Glyceryl Stearate, Cetearyl Alcohol, PEG-40, Cetrimonium Chloride, Hydrolyzed Keratin, Panthenol, DM DM Hydantoin, Methylparaben, Propylparaben, Tetrasodium EDTA and perhaps a fragrance.

EXAMPLE 1

| Chemical | Proposed Function | % by Weight |
|---|---|---|
| Water | | 80-99 |
| Vitamin E | Antioxidant/protectant Conditioner | 0.15-10 |
| Castor oil | Water-retainer/protectant | 0.2-3.0 |
| Stearalkonium chloride | Conditioner/anti-static | 2.0-10 |
| PEG 40 Castor Oil | Emulsifier/conditioner | 0.2-5 |
| Hydrolyzed keratin | Hair protein | 0.2-3.0 |
| EDTA tetra sodium Salt | Chelating agent | 0.1-2 |
| Methyl/propylparaben | Preservative | 0.1-3 |
| Panthenol | Emulsifier/surfactant | 0.1-4 |
| Glycerol Stearate | Moisturizer | 0.1-10 |
| Cetearyl Alcohol | Emulsifier/surfactant | 0.1-5 |
| Cetrimonium Chloride | Emulsifier/surfactant | 0.1-5 |

Parabens are esters of para-hydroxybenzoic acid, from which the name is derived. Common parabens include methylparaben, ethylparaben, propylparaben and butylparaben. Less common parabens include isobutylparaben, isopropylparaben, benzylparaben and their sodium salts. The general chemical structure of a paraben is depicted as chemical structure I, with R representing an alkyl group such as methyl, ethyl, propyl or butyl.

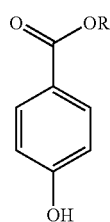

Structure I

Natural vitamin E exists in eight different forms, four tocopherols and four tocotrienols. All feature a chromanol ring, with a hydroxyl group that can donate a hydrogen atom to reduce free radicals and a hydrophobic side chain which allows for penetration into biological membranes. Both the tocopherols and tocotrienols occur in alpha, beta, gamma and delta forms, determined by the number of methyl groups on the chromanol ring. Each form has slightly different biological activity.

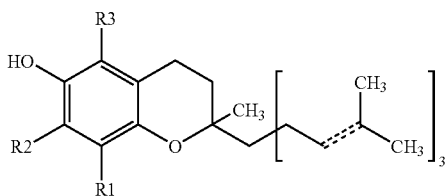

α-tocopherol

α-tocopherol is traditionally recognized as the most biological antioxidant in humans. The measurement of "vitamin E" activity in international units (IU) was based on fertility enhancement by the prevention of spontaneous abortions in pregnant rats relative to α tocopherol. It increases naturally to about 150% of normal in the maternal circulation during human pregnancies.

Other R, R, R Tocopherol

The other R, R, R tocopherol vitamins are slowly being recognized as research begins to elucidate their additional roles in the human body. Many naturopathic and orthomolecular medicine advocates suggest that vitamin E supplements contain at least 20% by weight of the other natural vitamin E isomers. According to the present invention, the term "Vitamin E salt" shall be understood to comprise all tocopherol isomers, whether natural or unnatural, in any combination and any organic or inorganic salt.

Castor Oil shall be understood to include chemicals according to the structure:

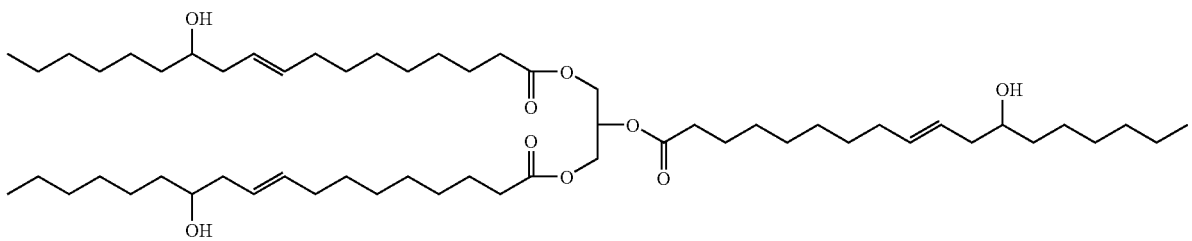

including isomers, racimates and salts.

Castor Oil is unique among all fats and oils in that:
- it is the only source of an 18-carbon hydroxylated fatty acid with one double bond.
- ricinoleic acid (12-Hydroxyoleic Acid) comprises approximately 90% of the fatty acid composition.
- product uniformity and consistency are relatively high for a naturally occurring material
- it is a nontoxic, biodegradable, renewable resource. The remarkably constant composition of castor oil fatty acids is shown below:

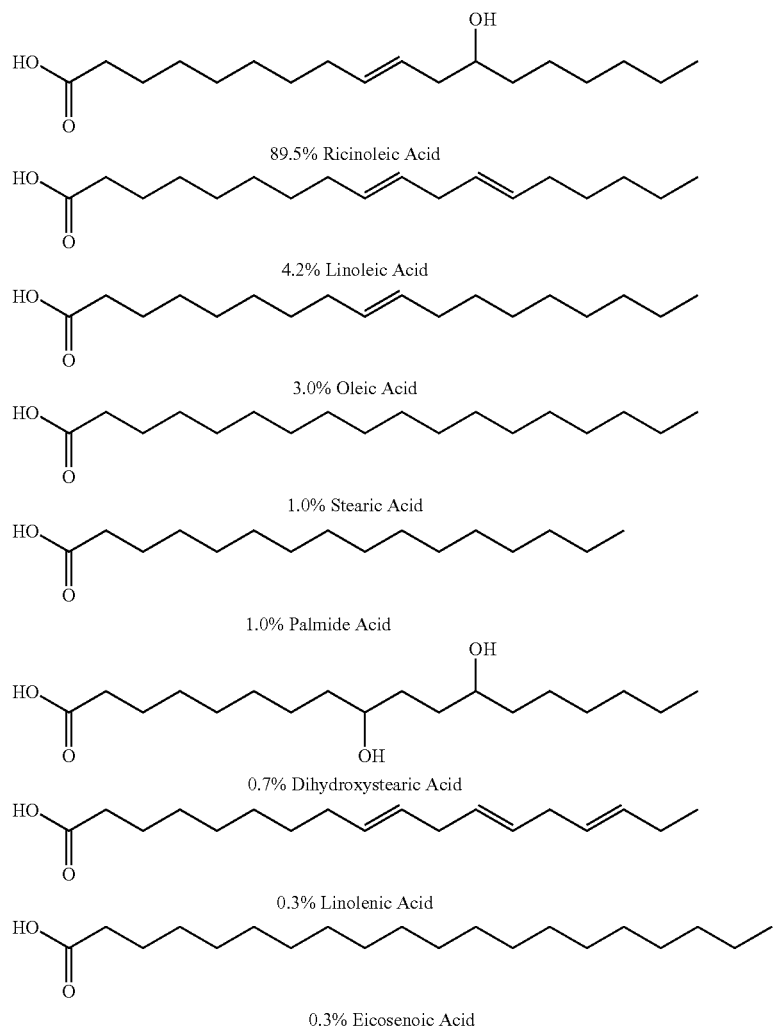

89.5% Ricinoleic Acid
4.2% Linoleic Acid
3.0% Oleic Acid
1.0% Stearic Acid
1.0% Palmide Acid
0.7% Dihydroxystearic Acid
0.3% Linolenic Acid
0.3% Eicosenoic Acid The hydroxyl groups in castor oil account for a unique combination of physical properties:
Relatively high viscosity and specific gravity;
Solubility in alcohols in any proportion;
Limited solubility in aliphatic petroleum solvents.

The uniformity and reliability of its physical properties are demonstrated by the long-term use of castor oil as an absolute standard for viscosity. Because of its higher polar hydroxyl groups, castor oil is not only compatible with but will plasticize a wide variety of natural and synthetic resins, waxes, polymers and elastomers. Castor Oil also has excellent emollient and lubricating properties as well as a marked ability to wet and disperse dyes, pigments and fillers. In the form of its chemical derivatives, castor oil's application versatility is further enhanced.

| | Composition for Hair and Body Application | | |
|---|---|---|---|
| | Nature of Reaction | Added Reactants | Type of Products |
| Ester Linkage | Hydrolysis | Acid, enzyme, or Twitchell reagent catalyst | Fatty acids, glycerol |
| | Esterification | Monohydric alcohols | Esters |
| | Alcoholysis | Glycerol, glycols, pentaerythritol, etc. | Mono- and diglycerides, monoglycols, etc. |
| | Saponification | Alkalies, alkalies plus metallic salts | Soluble soaps, insoluble soaps |
| | Reduction | Na reduction | Alcohols |
| | Amidation | Alkyl amines, alkanolamines, etc. | Amine salts, amides |
| | Halogenation | $SOCl_2$ | Fatty Acid halogens |
| Double Bond | Oxidation, Polymerization | Heat, oxygen, crosslink agent | Polymerized oils |
| | Hydrogenation | Hydrogen (moderate pressure) | Hydroxystearates |
| | Epoxidation | Hydrogen peroxide | Epoxidized oils |
| | Halogenation | $Cl_2$, $Br_2$, $I_2$ | Halogenated oils |
| | Addition Reactions | S, maleic acid | Polymerized oils |
| | Sulfonation | $H_2SO_4$ | Sulfonated oils |

| | Composition for Hair and Body Application | |
|---|---|---|
| Nature of Reaction | Added Reactants | Type of Products |
| Hydroxyl Group Dehydration, | Catalyst (plus heat) | Dehydrated castor oil, |
| Hydrolysis, distillation | | Octadecadienoic acid |
| Caustic fusion | NaOH | Sebacic acid, capryl alcohol |
| Pyrolysis | High heat | Undecylenic acid, heptaldehyde |
| Halogenation | $PCl_5$, $POCl_3$ | Halogenated castor oils |
| Alkoxylation | Ethylene and/or propylene oxide | Alkoxylated castor oils |
| Esterification | Acetic-, phosphoric-, maleic-, phthalic anhydrides | Alkyl and alkylaryl esters, phosphate esters |
| Sulfation | $H_2SO_4$ | Sulfated castor oil (Turkey red oil) |
| Urethane reactions | Isocyanates | Urethane polymers |

Another embodiment of the present invention, the formula for which is provided in Example 2 below, is a rebuilder that may be used on humans as well as horses and other domestic animals, such as dogs and cats. In humans, the rebuilder makes the hair thirty percent stronger so that less hair falls out and the hair will be thicker and fuller. The present invention has been used by chemotherapy patients and by people who are experiencing hair loss due to high blood pressure medication. The present invention has been found to make finger nails thirty percent stronger, and may be used as a moisturizer for dry, calloused hands. In pets, the rebuilder strengthens and repairs dry, damaged coats and cracked paw pads, and corrects the structure of weakened, dry damaged coats and paw pads. The rebuilder stimulates and promotes rapid hair and paw pad repair without the use of silicone, synthetic polymers or petroleum based products. The rebuilder binds protein to the coat, returning elasticity and restoring strength, removing damaging toxins, medications, and chemical residues. It detangles severely matted hair and is safe to use on dry noses. In horses, it strengthens hair so the mane and tail won't break off easily and it makes the hair healthier and stronger. It also makes hooves grow from 10% to 50% faster and makes them 30% stronger. Sand cracks are reduced, quarter cracks heal faster, and shoes hold better. The composition is especially helpful for treating shelly-footed horses. The rebuilder is environmentally friendly and non-toxic.

The compositions of the present invention may also contain as adjuvant materials various substances, such as vitamins, lanolin or its derivatives, bactericides, plant extracts, coloring agents, perfumes, thickeners, buffers, surface active agents, and sequestering agents.

EXAMPLE 2

A composition for rebuilding or repairing tissue, such as hair, skin nails, Or horse's hooves is prepared by mixing the following formulation which is created in two phases: oil and water, which are then combined to produce 250 gallons of liquid.

| Chemical | Function | Quantity | % by Weight |
|---|---|---|---|
| Water Phase | | | |
| Deionized Water | carrier | 204 gallons/ 1700 lbs | 81.4 |
| Methylparaben | preservative | 2.1 lbs | 0.10 |
| Versene ® | chelating agent | 2.1 lbs | 0.10 |
| Stearalkonium Chloride | conditioner/ anti-static | 177.5 lbs | 8.50 |
| Cetrimonium Chloride | conditioner | 20.9 lbs | 1.00 |
| Oil Phase | | | |
| Cetearyl Alcohol | emulsifier | 52.2 lbs | 2.50 |
| Glyceryl Stearate | emulsifier | 73.1 lbs | 3.50 |
| PEG 40 Castor Oil | emulsifier | 31.3 lbs | 1.50 |

| Composition for Hair and Body Application | | | |
|---|---|---|---|
| Propylparaben | preservative | 1 lbs | 0.05 |
| Vitamin E Acetate | antioxidant | 3.1 lbs | 0.15 |
| Panthenol | vitamin | 4.2 lbs | 0.20 |
| Hydrolyzed Keratin Protein | protein | 6.2 lbs? | 0.30 |
| DMDM Hydantoin | preservative | 4.2 lbs | 0.2 |
| Coconut Fragrance | fragrance | 10.4 lbs | 0.50 |
| Pineapple Fragrance | fragrance | | |
| Total Volume/Weight | | 250 gal/ 2,088 lbs | | verseneR is tetrasodium EDTA, a chelating agent that is commercially available from The Dow Chemical Company, Midland7 MI. PEG 40 Castor Oil is a castor oil derivative and an emulsifier available from a number of chemical suppliers including Lambert Technologies Corp., Gumee, Ill.

While the invention has been described in connection with one or more preferred embodiments, such embodiments are not intended to limit the scope of the invention to the particular form set forth, but, is intended to cover such alternatives, modifications, and equivalents as may be included within the spirit and scope of the invention as defined in the appended claims.

What is claimed is:

1. An oil and water composition for repairing hair, skin, nails or hooves consisting of a water phase and an oil phase, wherein the water phase consists of:
   deionized water in an amount of 81.4% by weight;
   methylparaben in an amount of 0.1% by weight;
   tetrasodium EDTA in the amount of 0.1% by weight;
   stearalkonium chloride in an amount of 8.5% by weight; and
   cetrimonium chloride in an amount of 1% by weight; and wherein the oil phase consists of:
   cetearyl alcohol in an amount of 2.5% by weight;
   glyceryl stearate in the amount of 3.5% by weight;
   PEG 40 castor oil in the amount of 1.5% by weight;
   propylparaben in the amount of 0.05% by weight;
   Vitamin E acetate in the amount of 0.15% by weight;
   panthenol in an amount of 0.2% by weight;
   hydrolyzed keratin protein in an amount of 0.3% by weight;
   DMDM hydantoin in an amount of 0.2% by weight; and
   fragrance in an amount of 0.5% by weight, wherein the fragrance is coconut and/or pineapple.

* * * * *